United States Patent [19]
Moberg

[11] Patent Number: 5,265,607
[45] Date of Patent: Nov. 30, 1993

[54] PATIENT MONITORING ELECTRODE CONNECTION APPARATUS AND METHOD

[75] Inventor: Richard Moberg, Philadelphia, Pa.
[73] Assignee: Moberg Medical, Inc., Ambler, Pa.
[21] Appl. No.: 782,536
[22] Filed: Oct. 25, 1991
[51] Int. Cl.$^5$ .............................................. A61N 1/08
[52] U.S. Cl. ..................................... 128/639; 128/731
[58] Field of Search ................................ 128/639, 731

[56] References Cited

U.S. PATENT DOCUMENTS

| | | | |
|---|---|---|---|
| 2,409,033 | 10/1946 | Garceau | 128/731 |
| 2,712,309 | 7/1955 | Offner | 128/731 |
| 3,027,419 | 3/1962 | Owen et al. | 128/731 |
| 3,760,796 | 9/1973 | Baessler et al. | 128/731 |
| 4,094,307 | 6/1978 | Young, Jr. | 128/731 |

Primary Examiner—William E. Kamm
Assistant Examiner—Scott M. Getzow
Attorney, Agent, or Firm—Reed Smith Shaw & McClay

[57] ABSTRACT

A headbox for connecting patient monitoring physiological sensors to a monitoring instrument, such as an EEG machine, includes a general purpose input/output device having connectors for coupling to the sensors and to the instruments, which is configured for a particular monitoring procedure by one of a plurality of similar configuration cards which are electrically and mechanically compatible with the input/output device. The configuration card includes interconnections between the sensors and the instrument inputs which are specific for a particular monitoring procedure. The configuration card may include a graphic representation of a body to show where sensors should be placed on a patient and connected to the headbox for the particular monitoring procedure, and may physically occlude connectors which are not to receive sensors in the procedure. The configuration card may include a memory for storing data regarding a patient or the monitoring procedure for which it is configured.

42 Claims, 8 Drawing Sheets

PATIENT MONITORING ELECTRODE CONNECTION APPARATUS AND METHOD

FIELD OF THE INVENTION

This invention relates to the field of medical instrumentation and patient monitoring. More specifically, this invention relates to the field of physiological signal recording and processing. Still more particularly, this invention relates to methods and apparatus for connecting physiological sensors to instruments which process the output of such sensors.

BACKGROUND OF THE INVENTION

In medicine and physiology, sensing electrodes are frequently connected to monitoring instruments which record, analyze, display, process, or otherwise monitor physiological signals generated by such sensing electrodes. Sensing electrodes are placed at specific locations on a patient's body to sense signals occurring at such locations, and coupled to an appropriate monitoring instrument to produce useful physiological output information such as an electrocardiogram (ECG), electroencephalogram (EEG), or electromyogram (EMG).

The present invention is particularly but not exclusively useful in encephalograhic or brain wave monitoring using electrodes attached to a patient's head and connected to an EEG machine, which is a monitoring instrument used for the analysis and display of signals generated by such sensing electrodes. In this application, the connection of the sensing electrodes to the monitoring instrument is made through a connection box commonly called a "headbox" since it is located near the patient's head. Sensing electrode assemblies used for EEG typically comprise a metal disk which is glued to a patient's head or a needle which is inserted into a patient's head subcutaneously. The disk or needle is connected to one end of a wire conductor which has a connector portion such as a standard pin plug connected to the other end of the conductor. This connector portion is adapted to be detachably connected to a mating connector portion in the headbox, such as a jack which mates with a pin plug. Such electrode assemblies are referred to typically and herein as "electrodes." Also in this disclosure, both connector portions and the connector assembly formed when such portions are mated may be referred to as "connectors." Such connectors include conductors in each portion which contact mating conductors in order to couple signals present on one connector portion to the mating connector portion.

In conventional apparatus, the headbox is merely a box with connectors such as electrical jacks which receive electrode connectors such as standard pin plugs. The headbox may have a stylized picture of a head on it to indicate which electrode pin plug is to be placed into which jack. Headboxes may also have pre-amplifiers contained within them which amplify the low voltage EEG signals for transmission along a cable from the headbox output to the input in the monitoring instrument.

EEG machines are large, complicated instruments and thus are desirably operated by trained technologists. In the prior art, the headbox used with such machines is typically connected to a switch panel on the EEG machine having an array of switches which allows connection of any electrode to any channel input of the EEG machine This array of switches may be controlled manually or by computer software. EEG technologists are trained as to where to place electrodes on a patient's head, how to switch the electrodes into the EEG machine input channels, and how to set up the EEG machine for the particular medical procedure being performed.

Brain wave monitoring is increasingly being performed by physicians and hospital personnel who are not specifically trained in electroencephalography. Examples of such monitoring include surgical monitoring, where the EEG machine is typically operated by an anesthesiologist, and in intensive care units (ICU's) where the EEG machine may be operated by a nurse. In these settings, it is extremely important to make the operation of the brain monitoring equipment as easy as possible so that appropriate and accurate monitoring is accomplished.

Conventional EEG machines and more specialized brain wave monitors are difficult to use by those not trained in EEG technology, in part due to the setup procedures involved. Such difficulties associated with EEG monitoring procedures include selecting the number of electrodes and determining the correct location for their attachment to the body for each different monitoring procedure; switching the electrodes into the correct monitoring instrument inputs for each different monitoring procedure; setting up the monitoring instrument for the correct processing and displays for each different monitoring procedure; and having to set up another monitor with the same parameters when the patient is moved from one room to another room or from the operating room ("OR") to the ICU. Similar difficulties also are found in other types of monitoring such as ECG and EMG monitoring.

SUMMARY OF THE INVENTION

It is therefore a general object of the invention to provide an improved apparatus and method for connecting electrodes to a patient monitoring instrument.

It is a more specific object of the invention to provide an electrode connection method and apparatus which renders proper electrode connection easier and more reliable than in the prior art.

It is an object of the invention to provide an electrode connection method and apparatus which enables a user to quickly determine the number and placement of electrodes required for a particular patient monitoring procedure.

It is another object of the invention to provide an electrode connection method and apparatus which facilitates connection of electrodes to the proper inputs of patient monitoring instruments for particular monitoring procedures.

It is another object of the invention to provide an electrode connection method and apparatus which facilitates continued proper monitoring when a patient is moved from one monitoring instrument to another.

In accordance with these objects, apparatus of the preferred embodiment of the present invention includes a headbox having a housing including an array of electrode jacks mounted therein, and a configuration card adapted to be cooperatively associated with the housing to identify particular jacks which are to receive electrodes in the procedure for which the configuration card is configured. The configuration card includes means for connecting predetermined jacks to predetermined headbox outputs in accordance with a particular monitoring procedure for which the card is configured. The configuration card desirably includes indicia identifying the locations on the patient's head at which electrodes are to be placed in performing the monitoring procedure for which the configuration card is configured. The headbox may further include amplifier means for amplifying electrode signals, and memory means for storing information relating to the monitoring procedures.

The method of the present invention comprises providing an interconnection apparatus having a plurality of inputs adapted to receive physiological signals from electrodes and a plurality of outputs adapted to be coupled to input channels of a monitoring instrument, and configuring the interconnection apparatus for a particular patient monitoring procedure by coupling predetermined inputs to be used in the monitoring procedure to predetermined outputs of the apparatus. The configuration step may include disabling inputs which are not to be used in the patient monitoring procedure. In the preferred method, the configuring step includes coupling one of a plurality of configuring devices to a general-purpose programmable interconnection apparatus to form an interconnection apparatus which is programmed or configured for a particular monitoring procedure and/or patient. The method of the present invention may further include storage of information relating to the monitoring procedure and/or the patient being monitored.

Other objects and features of the present invention will become apparent upon review of the following specification and the drawings.

DETAILED DESCRIPTION

Figure 1:
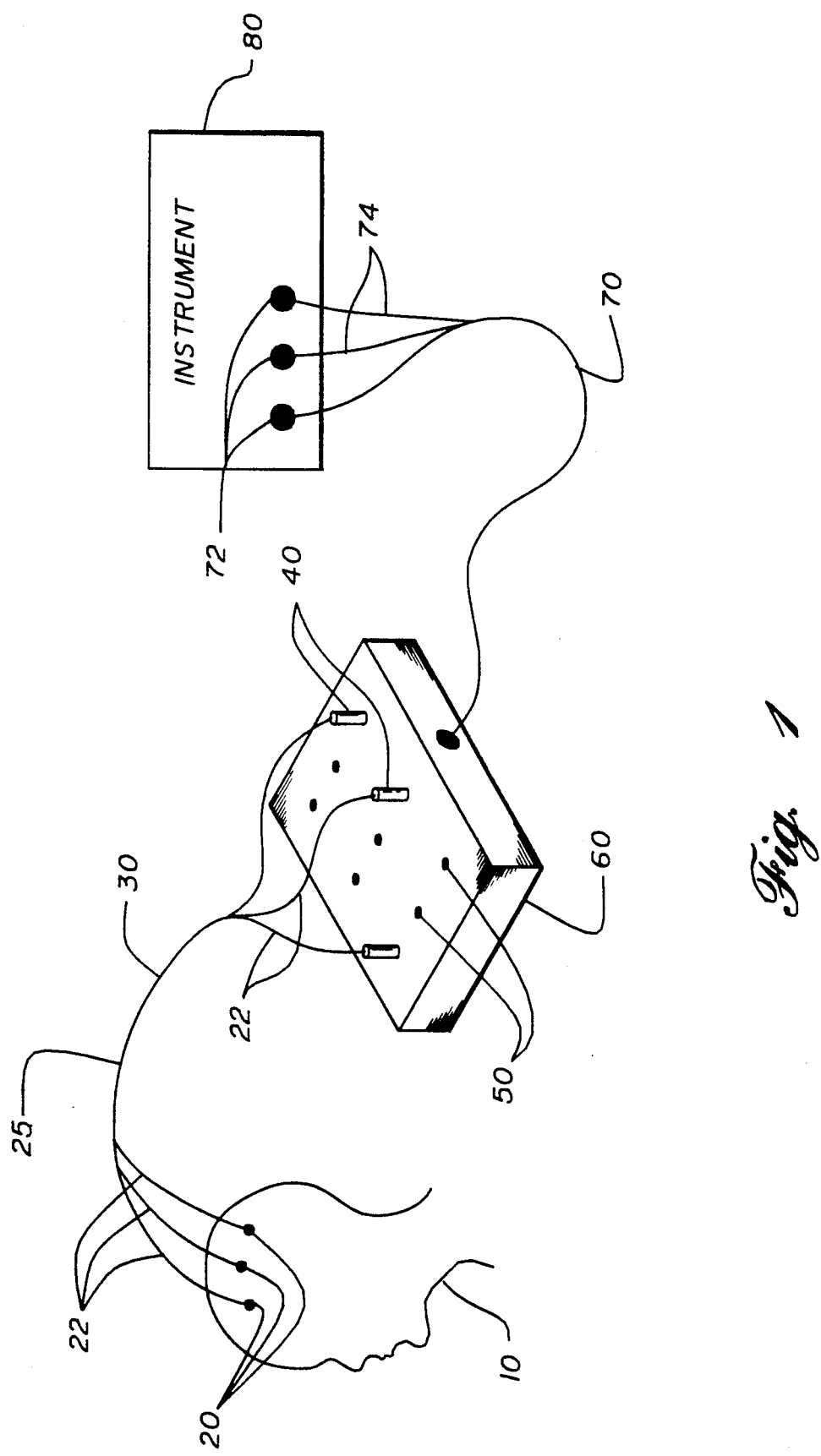
FIG. 1 is an illustration of the environment in which the present invention is used.

FIG. 1 illustrates the EEG monitoring environment in which the method and apparatus of the present invention may be used. More specifically, FIG. 1 shows components used in electroencephalographic monitoring. A patient 10 is fitted with one or more sensing electrodes 20 which are affixed to the patient's scalp for generation of EEG signals. Each sensing electrode 20 is typically affixed to a predetermined area of the patient's head, and together with a ground or reference electrode, each sensing electrode 20 constitutes the transduction means for one channel of EEG data. A plurality of such sensing electrodes 20 is commonly affixed to the patient's scalp, and multiple channels of EEG data are acquired, processed, and recorded and/or displayed during EEG monitoring.

Each sensing electrode 20 is connected to one end of a wire or conductor 22, and a connector such as a standard pin plug connector 40, comprising conductive means for coupling signals present on conductor 22 to a mating conductor, is connected to the other end of each such wire 22. Each such assembly comprising a sensing electrode 20, a wire 22, and a connector 40 is commonly referred to as an "electrode". The conductors 22 associated with each of the electrodes may comprise portions of a cable 30, in which event the collection of electrodes forms an electrode assembly 25.

A headbox 60 is provided, which includes a plurality of connectors such as jacks 50. Such connectors are adapted to mate with connectors 40 of the electrodes and include conductive means for contacting mating conductors of connectors 40 for receiving any physiological signals present at connectors 40. Headbox 60 thus receives physiological signals from all of the electrodes connected to the patient 10. A monitoring instrument 80 such as an EEG machine is provided, which includes a plurality of inputs 72 for receiving physiological signals, such as various channels of EEG data. Headbox 60 is provided to enable interconnection and coupling of predetermined electrodes to predetermined monitoring instrument inputs 72 in accordance with the characteristics of monitoring instrument 80 and the particular monitoring procedure to be performed. Typically, EEG data from one electrode is coupled to one input 72 of instrument 80 by one conductor 74 of a multiconductor cable 70 coupled between headbox 60 and instrument 80. Connectors to make cable 70 detachably securable to either headbox 60 or instrument 80, or both, may be provided at the appropriate end(s) of cable 70.

While the prior art headbox is a unitary and general purpose device, the headbox of the present invention comprises a plurality of components which are cooperatively associated or assembled to provide a headbox which is configured for a particular monitoring procedure. The monitoring procedure for which the headbox is configured may be changed by changing one or more components of the headbox assembly. Desirably, the headbox assembly is a two component assembly, one component of which is a general-purpose input/output device having inputs for receiving sensor signals and outputs for coupling sensor-related signals to a monitoring instrument, which component may be used with any patient and monitoring procedure, and the other component of which may be selected and secured to the input/output device to configure or particularize the assembly for a particular monitoring procedure, monitoring instrument, and/or patient.

Figure 2B:
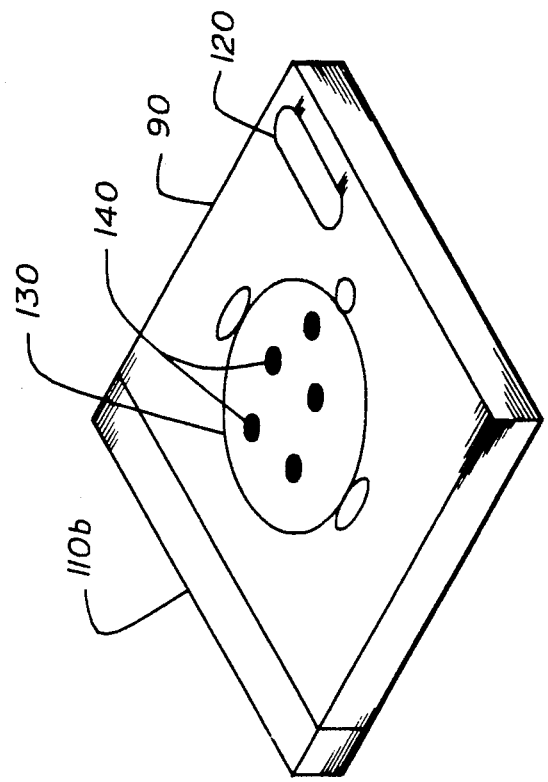
FIG. 2b is a perspective illustration of a configuration card portion of the headbox of the first embodiment.
Figure 2A:
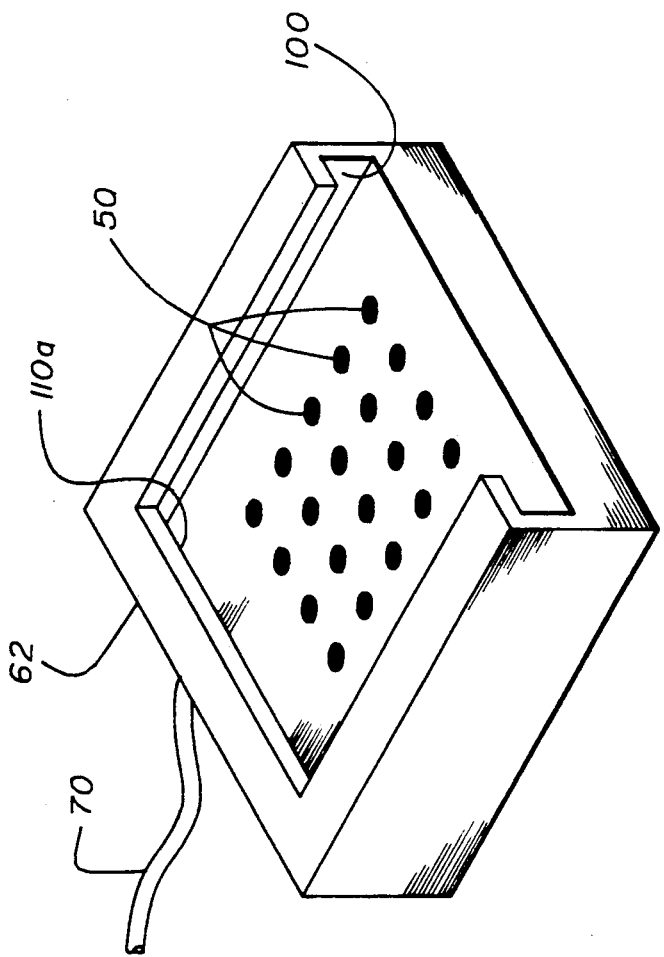
FIG. 2a is a perspective illustration of a housing portion of a first embodiment of the headbox of the present invention.

FIGS. 2a and 2b are perspective illustrations of components of a first embodiment of headbox 60 of the present invention. Headbox 60 includes a headbox housing 62, shown in FIG. 2a, and a configuration card 90, shown in FIG. 2b, which are detachably securable to each other. In accordance with the invention, the headbox housing 62 comprises a general-purpose input/output device, and configuration card 90 comprises a detachably securable configuration device. Headbox housing 62 includes an array of electrode jacks 50 mounted therein. Configuration card 90 and housing 62 are adapted to be assembled or cooperatively associated to form a headbox assembly 60. In the preferred embodiment shown in FIGS. 2a and 2b, the configuration card 90 slides into housing 62 via guide groves 100 to form a headbox assembly, but other means may be used to render a configuration card detachably securable to a headbox housing. Mounted within housing 62 is a multi-conductor electrical connector 110a, which is coupled (by means to be described more fully hereinafter) to the conductors of cable 70. A multi-conductor electrical connector 110b, which mates with connector 110a, is mounted to configuration card 90.

There are many applications for brain monitoring in surgery and in the intensive care unit. Each monitoring procedure requires that electrodes be placed in specific locations on the patient and that the monitoring instrument be configured in specific ways. A set of configuration cards 90 is provided in accordance with the present invention, each of which is electrically and mechanically compatible with housing 62 and is detachably securable thereto, but each of which is configured differently for use in one or more different types of monitoring procedure. Use of a configuration card designed for a particular procedure permits easy and reliable setup.

Each configuration card 90 desirably has a label 120 or other indicia specifying the type of monitoring procedure (surgical procedure, patient type, parameter to monitor for, etc.) for which the configuration card 90 is to be used. Configuration card 90 desirably has a graphic representation of a portion of a body, such as stylized representation of a head 130, to indicate where the electrodes are to be placed for the procedure specified on label 120.

In accordance with the first embodiment of the present invention, the configuration card includes means for specifying which jacks are to be used in the monitoring procedure and/or means for inhibiting the use of jacks which are not to be used in the procedure. As shown in FIG. 2b, configuration card 90 has one or more holes 140 through it, such holes being located adjacent each electrode jack to be used in the procedure specified on label 120 when configuration card 90 is inserted in headbox housing 62. Such holes provide a means for specifying which jacks are to be used in the procedure for which card 90 is configured. When configuration card 90 is mounted to headbox housing 62, it masks out or covers certain of the electrode jacks 50 which are not to be used during the specified monitoring procedure, and leaves accessible only those electrode jack locations which are to be used in the procedure. Such physical occlusion of unused jacks inhibits their use in the procedure, but other means for doing so may no doubt be employed.

The user of the apparatus selects a configuration card 90 appropriate for the procedure to be performed and secures it to a headbox housing 62. The user places sensing electrodes 20 on the patient's head in the locations specified by the head diagram 130 on configuration card 90. The user then connects the electrode plugs 40 of each electrode into the appropriate jacks 50 by passing them through the holes 140 in configuration card 90 corresponding to the indicated head location. In this manner, for each monitoring procedure, the user is informed as to where on the patient's head electrodes should be located and where on the headbox the corresponding plugs should be connected.

Figure 3:
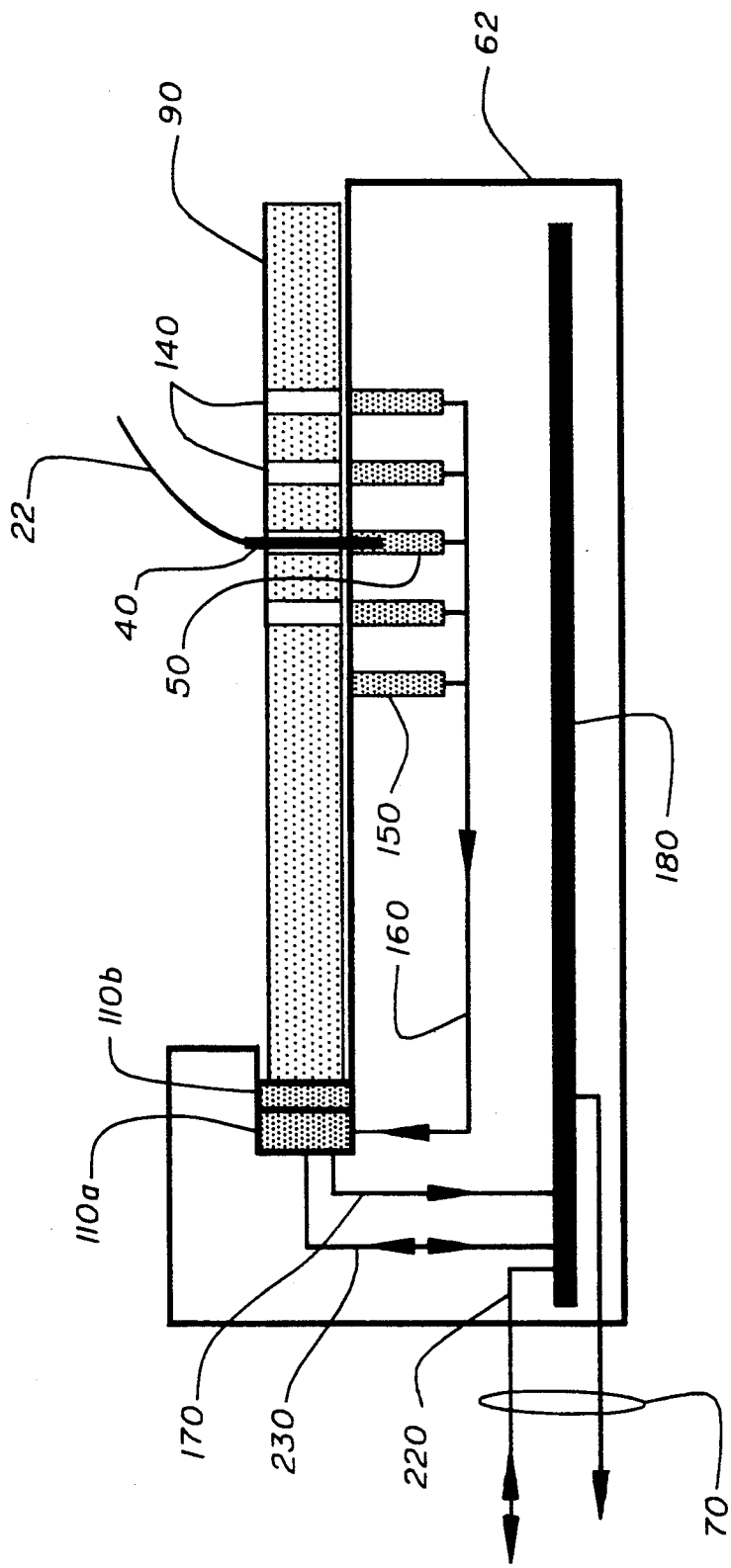
FIG. 3 is a partially schematic, partially cross sectional representation of the headbox of the first embodiment.
Figure 4:
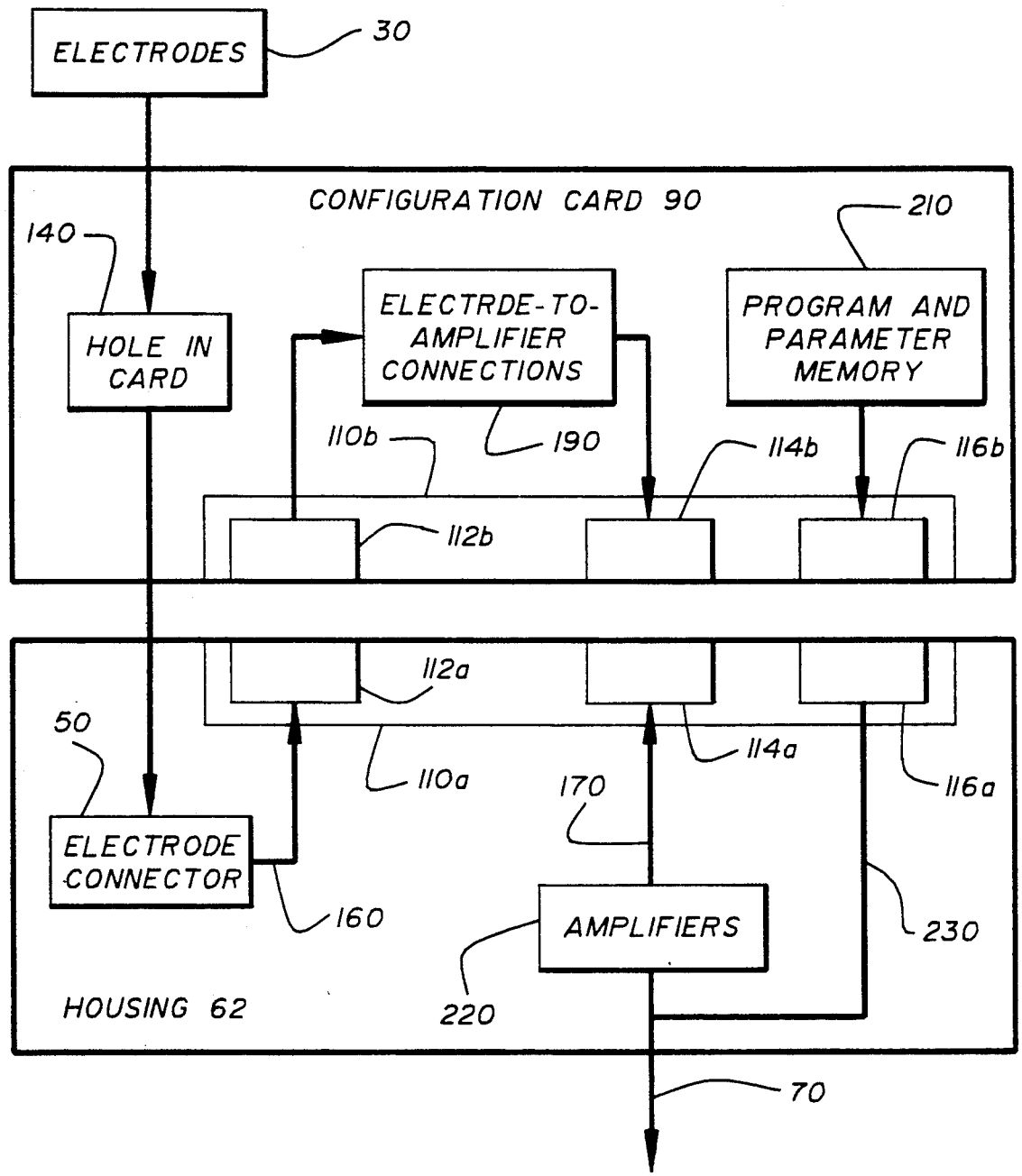
FIG. 4 is a schematic representation of the circuitry of the headbox of the first embodiment.

Having properly located electrodes on a patient's head and connected the associated plugs into specific jacks in the headbox, the electrical outputs from each of the electrodes must still be connected to the proper inputs of the instrument 80 for the specified monitoring procedure. FIGS. 3 and 4 show the preferred means for effecting such connection in the first embodiment.

FIG. 3 is a schematic cross section of the assembled headbox of the first embodiment, including a configuration card 90 mated with a headbox housing 62. Upon assembly of the headbox, connector portion 110b associated with the configuration card 90 is mated with connector portion 110a associated with housing 62. Connectors 40 such as pin plugs are inserted through the holes 140 in configuration card 90 into the connectors 50 adjacent the configuration card holes. No holes are provided in configuration card 90 adjacent to jacks 150 which are not to be used in the monitoring procedure associated with configuration card 90. Thus, configuration card 90 occludes or masks the connectors which are not to be used in the specified monitoring procedure and renders accessible only those connectors which are to be used in such procedure.

Each of the electrode jacks 50 (whether used or unused) is coupled to a contact of connector 110a by wires comprising cable 160. A set of mating contacts in connector 110b thus receives the EEG signals supplied to the set of jacks used in the particular monitoring procedure. In accordance with the present invention, these signals are desirably coupled to inputs of instrument 80 which are predetermined for each monitoring procedure but which may vary from procedure to procedure. In the apparatus illustrated in FIGS. 3 and 4, such connection is effected by subsets 112 and 114 of the contacts of connector 110 and by connection means 190. Connection means 190 comprises means for connecting each of the contacts 112b which are used in the procedure to one of the contacts 114b of connector 110b. Connection means 190 may be implemented by using dedicated coupling conductors such as jumper wires or printed circuit traces; connections means 190 may also be implemented by programmable switch means for selectively coupling contacts 112b to contacts 114b. Contacts 114b mate with mating contacts 114a of connector 110a, which are coupled through connection means such as a cable 170 to multi-conductor cable 70 which couples headbox 60 to instrument 80. Signal conditioning circuitry 220 is desirably provided, and described more fully below. However, such circuitry need not be provided, and signals present on connector 114a may be connected directly to conductors of cable 70. Thus, connection means 190 determines which of the electrode jacks 50 will be coupled to particular conductors of cable 70. The specific connection scheme employed between contacts 112b and contacts 114b is determined by the monitoring procedure to be performed and the monitoring instrument to be used.

Figure 5:
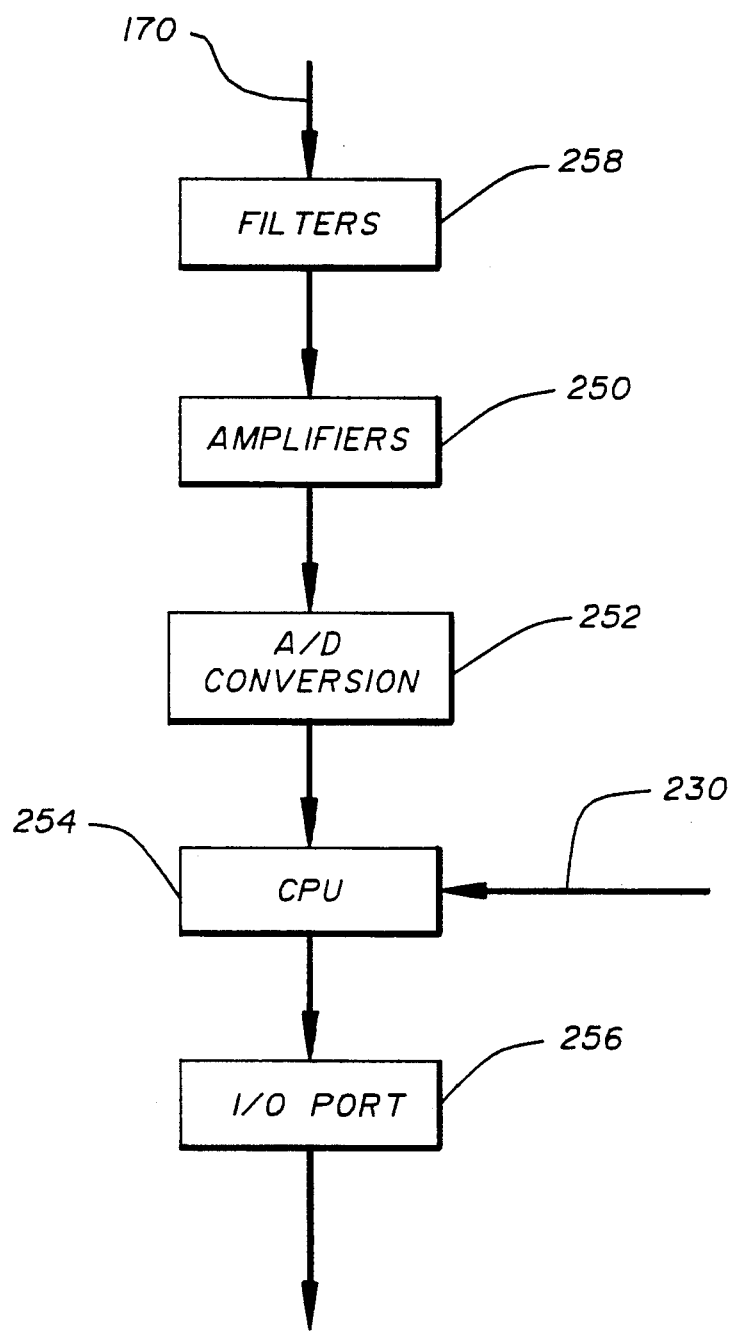
FIG. 5 is a block design of signal conditioning circuitry which may be included in the headbox of the present invention.
Figure 6B:
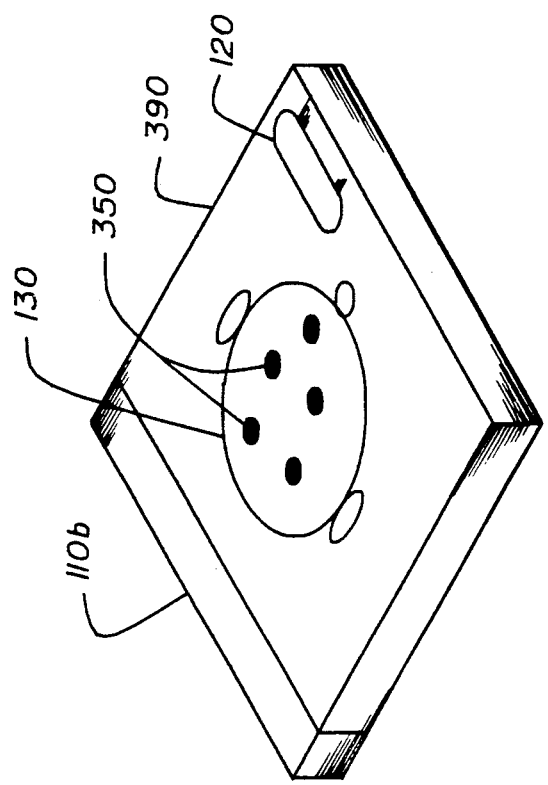
FIG. 6b is a perspective illustration of a configuration card portion of the headbox of the second embodiment.
Figure 6A:
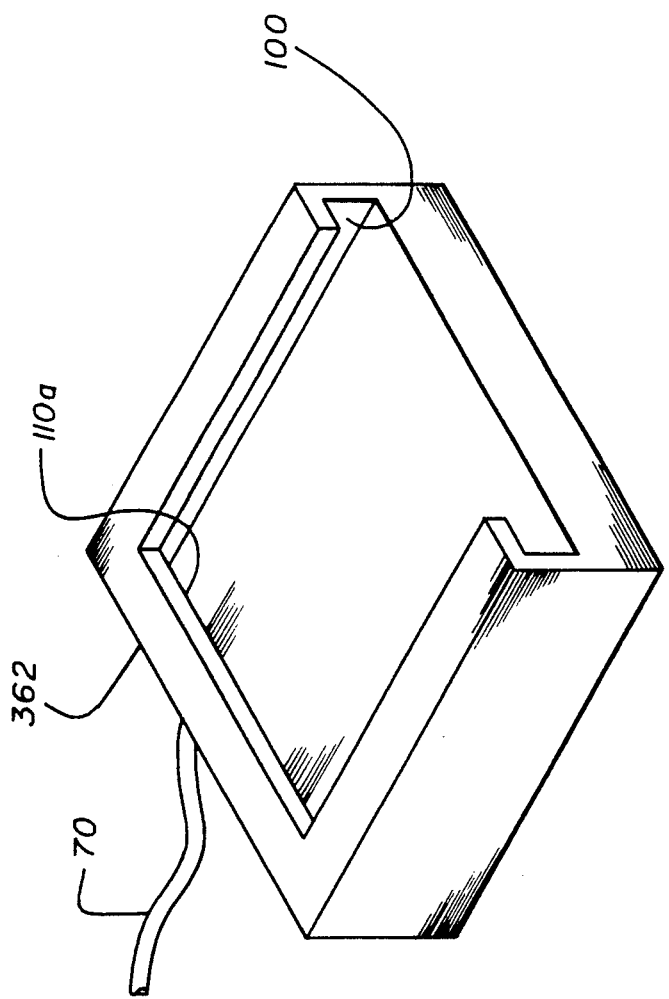
FIG. 6a is a perspective illustration of a housing portion of a second embodiment of the headbox of the present invention.
Figure 7:
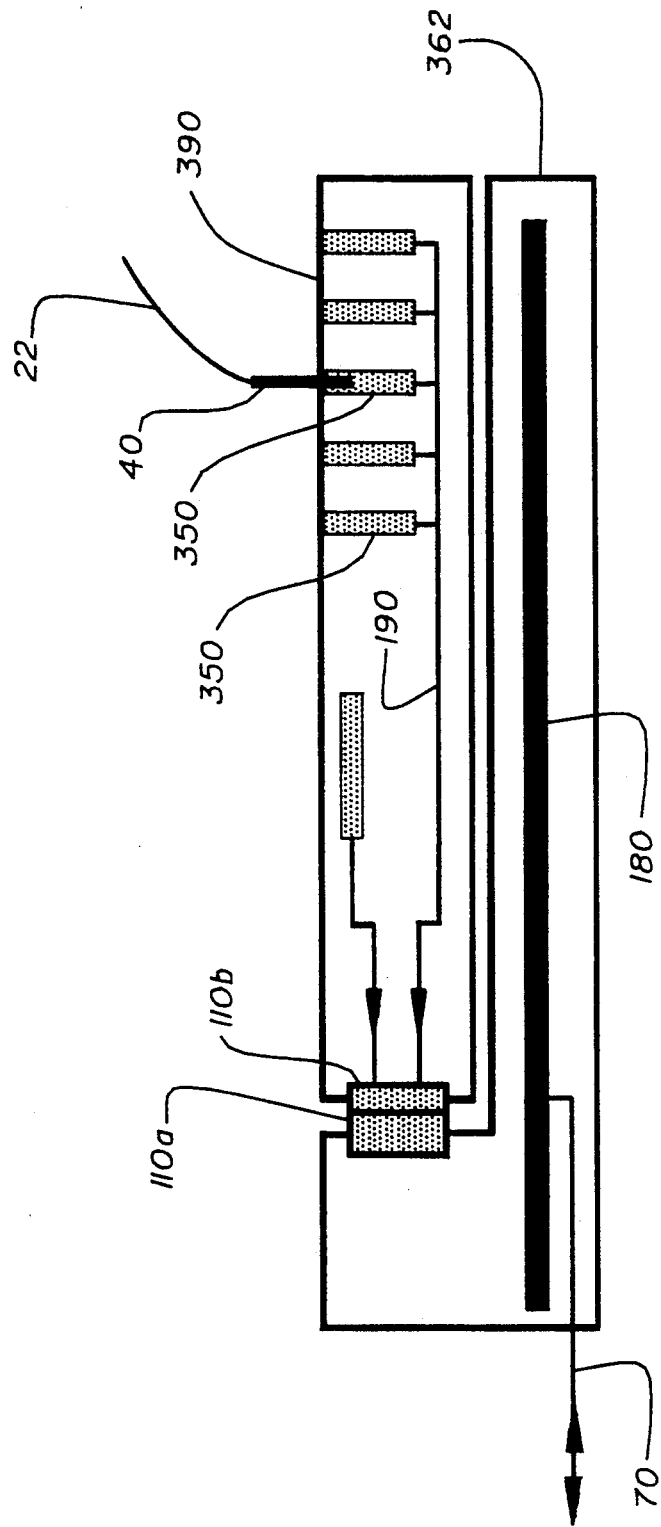
FIG. 7 is a partially schematic, partially cross sectional representation of the headbox of the second embodiment.
Figure 8:
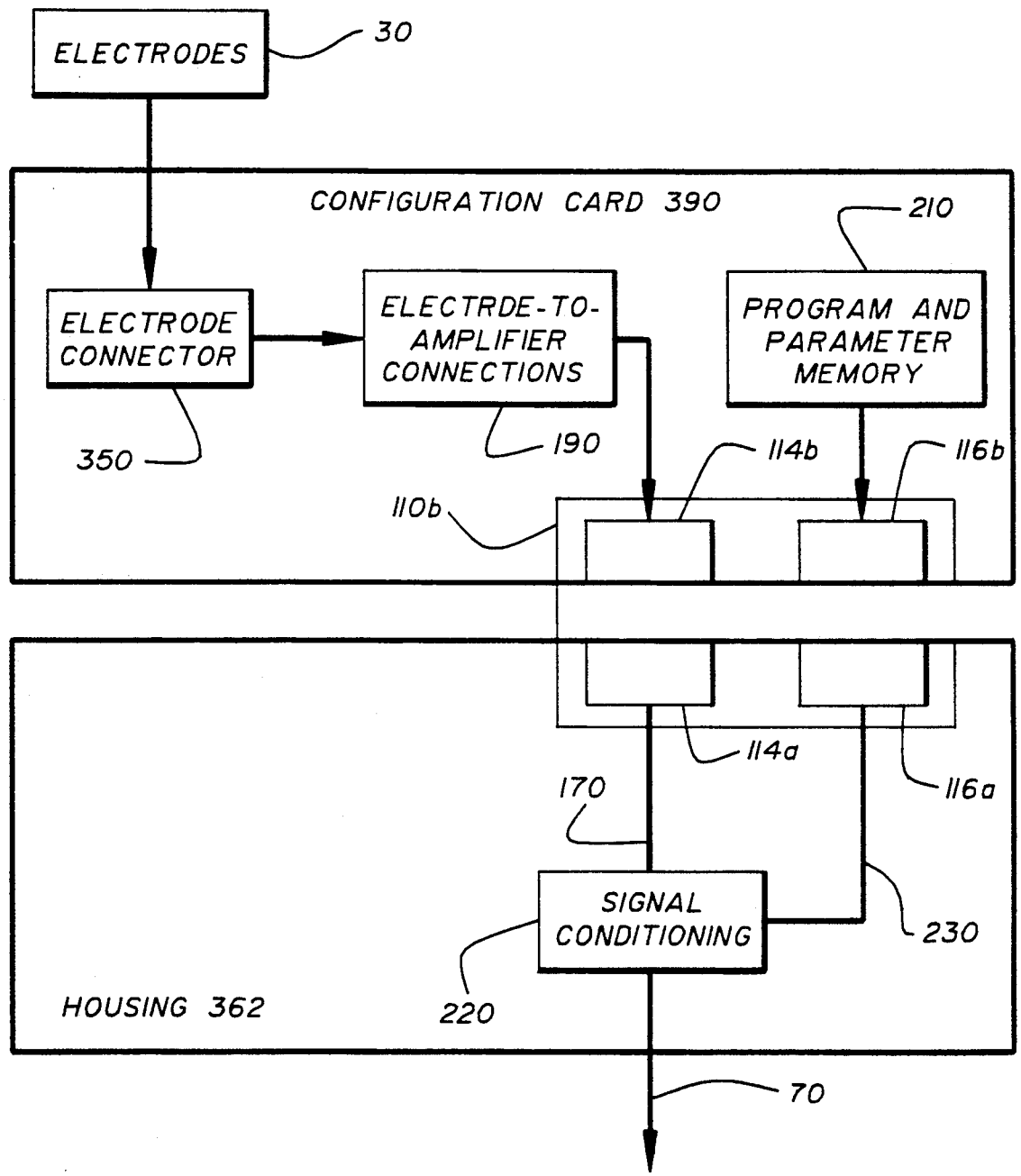
FIG. 8 is a schematic representation of the circuitry of the headbox of the second embodiment.

FIG. 5 shows various circuits which may be provided to process the neurological signals received by electrode jacks 50 in headbox 60 prior to transmission to monitoring instrument 80. Filters 258 may be provided to filter undesired signals from the electrode inputs. Signal conditioner 220 desirably includes one or more amplifiers 250, to amplify the low level neurological signals received at electrode jacks 50 for reliable transmission or further processing. Typically, one amplifier will be provided for each available channel.

Signal conditioner 220 may also comprise an A/D converter 252 for converting the analog neurological signals to digital form. As shown, A/D converter 252 is coupled to amplifiers 250 so that signals are amplified prior to conversion.

Converted digital signals relating to received analog neurological signals may be coupled from A/D converter 252 to a central processing unit ("CPU") 254, such as a microprocessor. CPU 254 is a part of a computer including memory and an I/O port 256. Such a computer may be provided for digital processing of signals prior to transmission (e.g. spectral analysis or filtering), to control communications of programs or data between headbox 60 and monitoring instrument 80, and the like. Control programs for operation of the computer may be stored in memory. Desirably such memory is protected against loss of stored information; this may be accomplished by a backup supply, or by use of static memory. I/O port 256 is provided to facilitate interchange of data between CPU 254 and monitoring instrument 80. I/O port 256 may be a standard port such as an RS-232 port.

It will be understood that not all of the various signal conditioning circuits described need be provided, and that the selection of such circuits or provision of additional signal conditioning circuits will in practice be made in accordance with the circumstances of the monitoring procedure to be performed and the capabilities of the monitoring instrument 80 to be used. For instance, signal conditioner 220 may consist solely of amplifiers 250; or A/D converter 252; or amplifiers 250 and A/D converter 252.

It will also be understood that signal conditioning circuitry 220 need not be located as shown, and may for instance be interposed in cable 160 or disposed in connection means 190. Also, rather than being provided in a single location as shown, the components of signal conditioner 220 may be disposed in different such locations. Applicant believes that implementation of the described signal conditioning function is well within the ordinary skill in the art and may be effected without undue experimentation.

FIG. 4 also illustrates another set of contacts 116 of connector 110, which are coupled to a program and parameter memory 210 that may be provided on the configuration card 90. Contacts 116a of connector 110a are coupled to conductors of cable 70 by cable 230. Program and parameter memory 220 may be accessed by monitoring device 80 through cables 70 and 230 and contacts 116 of connector 110. Program and parameter memory 210 may comprise conventional memory devices such as EEPROMS or programmable memory cards. Memory 210 may include a program memory specific to the monitoring procedure in which the configuration card 90 is to be used, and may contain instructions relating to the monitoring device 80 regarding the setup, data acquisition, processing, printout, display, and storage of incoming physiological data. Memory 210 may include a parameter memory to store data relating to a particular patient such as the patient's name, birth date, medical record number, and any changes from the normal set up of the instrument 80 to be used in monitoring the patient. By providing such a program and parameter memory 210, a configuration card 90 which has been set up for a particular patient and monitoring procedure may be removed from one headbox housing 62 and inserted into another headbox housing 62 associated with a different monitoring instrument 80, such as in a different room, to duplicate the settings of the original instrument. Thus, a configuration card may be moved with a patient in order to reliably and repeatedly duplicate previous monitoring conditions and patient data in any location to which the patient is moved.

Program and parameter memory is preferably located in the configuration card 90, so that it may accompany the patient over an extended period of time for monitoring in a variety of locations. However, in many situations, it may be desirable to move the entire headbox along with the patient. For instance, when a patient is moved from an OR to an ICU, it is desirable to leave the electrodes secured to the patient and coupled to the headbox, and to move the patient and the headbox as connected. Where the entire headbox is to accompany the patient, it is not necessary to locate the program and parameter memory 210 in the configuration card 90, and it may instead be located in the headbox housing 62 as shown in FIG. 4 by block 240.

FIGS. 6a, 6b, 7, and 8 show a second embodiment of a headbox of the invention, which is a modification of the first embodiment shown in FIGS. 2a, 2b, 3, and 4, respectively. Generally, the modification involves placing the connection jacks in the configuration card rather than the headbox housing. This makes it easier to transfer a patient from one monitoring instrument to another, since each monitoring instrument may be normally arranged with a headbox housing connected to it, and a patient may be disconnected from a first monitoring instrument by removing the configuration card from the first headbox housing, moved with the electrodes connected to the configuration card, and connected to a second monitoring instrument by inserting the configuration card into the headbox housing of the second instrument.

Elements which are the same in the first and second embodiments are indicated by like reference numerals. Configuration card 390, instead of holes, includes electrode jacks 350, preferably disposed at locations with respect to stylized head diagram 130 to indicate where on the patient each electrode should be located in performing the procedure intended for the card. Configuration card 390 mates with headbox housing 362 in order to form a complete headbox. Electrodes 30 are coupled to electrode connector jacks 350 in configuration card 390. Jacks 350 are coupled to contacts 114b of connector portion 110b by electrode-to-amplifier connection means 190. Signals from contacts 114b are coupled to signal conditioning circuitry 220 on circuit board 180 by mating contacts 114a and conductors 170. Conditioned signals are coupled to cable 70 for transmission to a monitoring instrument. A program and parameter memory 210 may also be disposed in configuration card 390 and coupled as previously described.

While preferred embodiments of the present invention have been described in detail, variations will no doubt occur to those skilled in the art without departing from the spirit and scope of the present invention.

What is claimed is:

1. Connecting apparatus for coupling each of a plurality of physiological sensors to one of a plurality of patient monitoring instrument inputs comprising a plurality of detachably securable components which may be assembled to form a complete connecting apparatus, including:

a plurality of input conductors, each of which is adapted to be detachably coupled to a physiological sensor; and connection means for connecting predetermined input conductors to predetermined output conductors, the connection of said input conductors to said output conductors being predetermined to configure said connecting apparatus for use in a predetermined patient monitoring procedure, wherein said apparatus includes means for indicating the locations on a patient at which said physiological sensors are to be placed in performing said predetermined patient monitoring procedure.

2. Connecting apparatus according to claim 1, wherein said apparatus consists of two detachably securable components.

3. Connecting apparatus according to claim 1, wherein said connection means is located in a different component of said apparatus than said input conductors or said output conductors.

4. Connecting apparatus according to claim 1, wherein said apparatus includes means for indicating which input conductors are to be coupled to physiological sensors in performing said predetermined patient monitoring procedure.

5. Connecting apparatus according to claim 1, wherein said means for indicating patient locations for physiological sensors includes a graphic representation of at least a portion of a human body.

6. Connecting apparatus according to claim 1, wherein said connection means includes a plurality of coupling conductors coupling said predetermined input conductors to said predetermined output conductors.

7. Connecting apparatus according to claim 1, wherein said connection means includes switch means for selectively coupling said input conductors to said output conductors.

8. Connecting apparatus according to claim 1, further comprising signal conditioning circuitry coupled to said input conductors.

9. Connecting apparatus according to claim 8, wherein said signal conditioning circuitry includes one or more amplifiers.

10. Connecting apparatus according to claim 8, wherein said signal conditioning circuitry includes an A/D converter.

11. Connecting apparatus according to claim 8, wherein said signal conditioning circuitry includes a central processing unit.

12. Connecting apparatus according to claim 1, further comprising memory means for storing data relating to said predetermined monitoring procedure and/or to a patient being monitored.

13. Connecting apparatus according to claim 12, further comprising means for coupling said memory means to said patient monitoring instrument.

14. Connecting apparatus according to claim 12, wherein said memory means is located in the same component of said apparatus as is said connection means.

15. Connecting apparatus according to claim 1, wherein said physiological sensors are coupled to a patient's head, and said patient monitoring instrument is an EEG machine.

16. Connecting apparatus for coupling each of a plurality of physiological sensors to one of a plurality of patient monitoring instrument inputs comprising a plurality of detachably securable components which may be assembled to form a complete connecting apparatus, including:

a plurality of input conductors, each of which is adapted to be detachably coupled to a physiological sensor; and connection means for connecting predetermined input conductors to predetermined output conductors, the connection of said input conductors to said output conductors being predetermined to configure said connecting apparatus for use in a predetermined patient monitoring procedure, wherein said apparatus includes means for inhibiting the coupling of physiological sensors to predetermined input conductors.

17. Connecting apparatus according to claim 16, wherein said means for inhibiting the coupling of physiological sensors to predetermined input conductors is located in the same component of said apparatus as is said connection means.

18. Apparatus for coupling each of a plurality of physiological sensors to one of a plurality of patient monitoring instrument inputs for performing a patient monitoring procedure comprising:

an input/output device, having a plurality of input connectors, each adapted to be detachably coupled to a physiological sensor, and having a plurality of output connectors, each adapted to be detachably coupled to a patient monitoring instrument input; and a plurality of configuration devices, each of which is detachably securable to said input/output device, each said configuration devices including connection means which, when said configuration device is secured to said input/output device, couples predetermined input connectors to predetermined output connectors in accordance with a predetermined patient monitoring procedure, wherein said each of configuration devices includes means for inhibiting the coupling of physiological sensors to predetermined input connectors.

19. Connecting apparatus according to claim 18, wherein said inhibiting means includes means for physically occluding said predetermined input connectors.

20. Connecting apparatus according to claim 18, wherein said coupling means includes switch means for selectively coupling input connectors to output connectors.

21. Connecting apparatus according to claim 18, wherein said input/output device includes signal processing circuitry coupled to said input connectors.

22. Connecting apparatus according to claim 21, wherein said signal conditioning circuitry includes one or more amplifiers.

23. Connecting apparatus according to claim 21, wherein said signal conditioning circuitry includes an A/D converter.

24. Connecting apparatus according to claim 21, wherein said signal conditioning circuitry includes a central processing unit.

25. Connecting apparatus according to claim 18, wherein said configuration devices include memory means for storing data relating to said predetermined patient monitoring procedure or to a patient being monitored.

26. Connecting apparatus for coupling each of a plurality of physiological sensors to one of a plurality of patient monitoring instrument inputs for performing a patient monitoring procedure comprising:

an input/output device, having a plurality of input connectors, each adapted to be detachably coupled to a physiological sensor, and having a plurality of output connectors, each adapted to be detachably coupled to a patient monitoring instrument input; and a plurality of configuration devices, each of which is detachably securable to said input/output device, each said configuration devices including connection means which, when said configuration device is secured to said input/output device, couples predetermined input connectors to predetermined output connectors in accordance with a predetermined patient monitoring procedure, wherein each of said configuration devices includes means for indicating the locations on a patient to which physiological sensors are to be placed in performing said predetermined patient monitoring procedure.

27. Connecting apparatus according to claim 26, wherein said means for indicating patient locations includes a graphic representation of at least a portion of a human body.

28. A method of coupling physiological sensors to a patient monitoring instrument for performing a monitoring procedure on a patient comprising:

providing an interconnection apparatus having a plurality of inputs connectors each adapted to be detachably coupled to a physiological sensor and a plurality of output connectors each adapted to be coupled to a patient monitoring instrument input;

configuring said interconnection apparatus for use in a predetermined monitoring procedure by coupling predetermined input connectors to predetermined output connectors; and coupling physiological sensors, attached to a patient in predetermined locations, to predetermined input connectors in accordance with indicia on said configuration device.

29. A method according to claim 28, wherein said configuring step includes securing to said interconnection apparatus a detachably securable configuration device having means for coupling said predetermined input connectors to said predetermined output connectors.

30. A method according to claim 28, further comprising the step of storing data in said interconnection apparatus relating to said monitoring procedure or to said patient.

31. A method according to claim 28, wherein said configuring step includes inhibiting connection of physiological sensors to predetermined input connectors.

32. A method according to claim 28, wherein said configuring step includes actuating switch means to selectively couple predetermined input connectors to predetermined output connectors.

33. Apparatus for supplying electrical signals derived from physiological sensors applied to a patient in a predetermined patient monitoring procedure to a monitoring instrument input comprising two detachably securable components, including:

a first component having a plurality of input conductors adapted to be coupled to physiological sensors, a first connector portion, and means for coupling said input conductors to said first connector portion in a manner which is predetermined in accordance with the patient monitoring procedure; and a second component having an output adapted to be coupled to said monitoring instrument input, a second connector portion which is detachably securable to said first connector portion, and means for coupling said second connector portion to said output.

34. Apparatus according to claim 33, wherein said first component is selected from a group of components, each of which may be secured to said second component to configure the apparatus for use in a different patient monitoring procedure.

35. Apparatus according to claim 33, further including means for indicating the locations on the patient at which physiological sensors are to be placed in performing the predetermined patient monitoring procedure.

36. Apparatus according to claim 35, wherein said means for indicating patient locations for physiological sensors includes a graphic representation of at least a portion of a human body.

37. Apparatus according to claim 33, further including a memory which is coupled to said output.

38. Apparatus according to claim 37, wherein said memory includes data relating to the predetermined patient monitoring procedure to be performed.

39. Apparatus according to claim 37, wherein said memory includes data relating to the patient upon whom the patient monitoring procedure is to be performed.

40. Apparatus according to claim 37, wherein said memory is located in said first component.

41. Apparatus according to claim 33, wherein said apparatus includes an analog-to-digital converter for supplying digital signals to said output which are derived from analog signals received at said input conductors.

42. Apparatus according to claim 41, wherein said analog-to-digital converter is located in said second component.

* * * * *